(12) United States Patent
McGann et al.

(10) Patent No.: US 7,880,137 B2
(45) Date of Patent: Feb. 1, 2011

(54) ELECTRODE DESIGN FOR AN ION SPECTROMETER

(75) Inventors: William J. McGann, Raynham, MA (US); Stephen L. Crook, Reading, MA (US)

(73) Assignee: Morpho Detection, Inc., Newark, CA (US)

( * ) Notice: Subject to any disclaimer, the term of this patent is extended or adjusted under 35 U.S.C. 154(b) by 430 days.

(21) Appl. No.: 11/966,179

(22) Filed: Dec. 28, 2007

(65) Prior Publication Data

US 2009/0166521 A1    Jul. 2, 2009

(51) Int. Cl.
*H01J 49/40* (2006.01)

(52) U.S. Cl. ......................... 250/287; 250/286
(58) Field of Classification Search ................. 250/288, 250/286, 287, 290
See application file for complete search history.

(56) References Cited

U.S. PATENT DOCUMENTS

| | | | |
|---|---|---|---|
| 5,200,614 A | 4/1993 | Jenkins | |
| 5,491,337 A | 2/1996 | Jenkins et al. | |
| 6,100,521 A * | 8/2000 | Doring et al. | 250/286 |
| 6,124,592 A | 9/2000 | Spangler | |
| 6,512,224 B1 | 1/2003 | Miller et al. | |
| 6,639,213 B2 | 10/2003 | Gillig et al. | |
| 6,690,004 B2 | 2/2004 | Miller et al. | |
| 6,690,005 B2 | 2/2004 | Jenkins et al. | |
| 6,727,495 B2 * | 4/2004 | Li | 250/286 |
| 6,815,669 B1 | 11/2004 | Miller et al. | |
| 6,831,273 B2 | 12/2004 | Jenkins et al. | |
| 6,914,241 B2 | 7/2005 | Giles et al. | |
| 6,943,343 B2 | 9/2005 | Honjo et al. | |
| 6,992,283 B2 | 1/2006 | Bateman et al. | |
| 7,071,465 B2 * | 7/2006 | Hill et al. | 250/286 |
| 7,075,068 B2 | 7/2006 | Miller et al. | |
| 7,095,014 B2 | 8/2006 | Hoyes | |
| 7,223,969 B2 | 5/2007 | Schultz et al. | |
| 7,256,396 B2 | 8/2007 | Reilly | |
| 7,547,880 B2 * | 6/2009 | Landgraf et al. | 250/287 |
| 2001/0032930 A1 * | 10/2001 | Gillig et al. | 250/288 |
| 2003/0132379 A1 * | 7/2003 | Li | 250/286 |
| 2007/0158548 A1 | 7/2007 | Haigh | |
| 2008/0073514 A1 * | 3/2008 | Landgraf et al. | 250/290 |

* cited by examiner

*Primary Examiner*—Jack I Berman
*Assistant Examiner*—Johnnie L Smith
(74) *Attorney, Agent, or Firm*—Armstrong Teasdale LLP

(57) ABSTRACT

Apparatuses and method are provided. For example, in one embodiment, a ring electrode includes a plurality of sub-rings adapted to provide an electric field inside a spectrometer. The sub-rings have an internal sub-ring radius. There is a ring insulator between adjacent sub-rings. Each said ring insulator has substantially the same internal radius as the sub-rings. In another embodiment, a method is provided for insertion of the ring electrode inside the spectrometer.

7 Claims, 3 Drawing Sheets

ELECTRODE DESIGN FOR AN ION SPECTROMETER

BACKGROUND OF THE INVENTION

1. Field of the Invention

Embodiments of the present invention generally relate to ion spectrometers, and more specifically to, a system, method, and apparatus for greater control over an ion spectrometer drift chamber.

2. Description of the Related Art

Ion mobility spectrometers have many applications, including security applications where the ion mobility spectrometer is used to search for unwanted substances (e.g., to identify explosives, narcotics, and other contraband).

Some prior art ion spectrometers acquire a sample by wiping a woven or non-woven fabric trap across a surface that is to be tested for molecules of interest. Other prior art ion spectrometers create a stream of gas adjacent the surface to be tested for the molecules of interest or rely upon an existing stream of gas.

FIG. 1 depicts a typical prior art ion mobility spectrometer 100. The ion spectrometer 100 includes a housing 102 (also known as a "bottle" 100); a gas inlet 106 (for receipt of a dopant (i.e., air in combination with ammonia and/or methylene chloride); a semi-permeable membrane 104; an inlet tube 118; an ionization chamber 114; radioactive source 116; electrodes 122, 124, 126, 128, 130, and 132; a drift region 112; an anode screen grid 134; an anode 136; and a gas exhaust 110.

When there is a chemical that needs to be identified, a sample of the chemical is taken. For example, a swab is wiped on an object containing the questionable chemical. The swab is placed against the semi-permeable membrane 104. The swab is then heated and the chemical(s) (e.g., explosives, narcotics, and the like) are turned into a vapor. The vapor permeates the membrane 104 while the membrane 104 helps to keep out contaminants (e.g., water).

An inlet tube 106 provides an inert gas (which includes air and a dopant (i.e., ammonia and/or methylene chloride)), which forces the vapor towards an ionization chamber 114. While in the ionization chamber 114, the vapor is exposed to a radioactive material 116 (i.e., nickel 63 or tritium). The radioactive material 116 bombards the vapor molecules with beta-particles and creates ions (i.e., charged molecules) from the vapor molecules.

A population of the ions builds up in the ionization chamber 114. An ion grid 120 separates the charged molecules from the drift region 112. The drift region 112 also includes a plurality of field-defining electrodes 122, 124, 126, 128, 130, and 132; and an anode screen grid 134 at the end of the drift chamber opposite the ionization chamber 114. Electrode 122 also includes a perforated ion grid 120 that, at the appropriate time, allows ions to pass through the perforations.

Electrodes 122, 124, 126, 128, 130, and 132 are each shaped like a disk. Because of their shape, electrodes 122, 124, 126, 128, 130, and 132 are referred to herein as "disk electrodes." "Disk shaped" as used herein is generally defined as a shape similar to a circular plate having a hole therethrough. The disk shape of the electrodes protrudes into the drift region 112 and has spaces there-between.

During manufacture of a spectrometer unwanted substances (e.g., cutting oil) can remain in the spectrometer. These unwanted substances often collect in the spaces between the disk shaped electrodes. In addition, after the spectrometer has analyzed a substance of interest, the analyzed substance of interest is no longer needed in the spectrometer and is considered an unwanted substance with respect to tests performed on subsequent substances of interest. The spaces between the disk shaped electrodes provide areas where the unwanted substances are trapped in the drift region. A "contaminant" as used herein is generally defined as any unwanted substance.

The impedance of the flow of ions can cause multiple problems. For example, during fabrication of the ion spectrometer, the spectrometer must be "burned in." The length of time for the burn in process is, in part, dependant upon the shape and configuration of the electrodes. The duration of the burn in time slows the manufacturing process. Other examples, a longer time to flush ions out of corners formed between the electrodes 122, 124, 126, 128, 130, and 132; and a non-uniform electric field (e.g., eddy currents) produced in the drift region 112.

After the ions have built up in the ionization chamber 114, a voltage is varied at the G1 electrode 122 to accelerate the ions through the ion grid 120 and into the drift region 112. The ions strike the anode 136 (also know as the collector electrode).

The anode 136 is coupled to an amplifier (not shown). The amplifier amplifies signals (i.e., ion currents) received by the anode 136. When a change in ion current is detected, the time that respective ions take to travel through the drift region 112 is measured. Larger ions move through the drift region 112 slower than smaller ions. The time taken to travel through the drift region 112 is used to derive the identity of the ions.

As the ions are analyzed, they are flushed out of the drift region 112 through a gas exhaust 110 and into a pump (not shown) and dryer (also not shown) for recycling of the dopant.

There is a need in the art for an improved electrode configuration that avoids the shortcomings and drawbacks of prior art systems and methodologies (e.g., which allows a shorter burn in time; a more uniform electric field; and easier flushing of contaminants).

SUMMARY

These and other deficiencies of the prior art are addressed by embodiments of the present invention, which generally relates to ion spectrometers, and more specifically to, apparatuses for greater control over an ion spectrometer drift chamber.

In one embodiment, a ring electrode includes a plurality of sub-ring shaped electrodes (hereinafter referred to as "sub-rings") adapted to provide an electric field inside a spectrometer. The sub-rings have an internal radius. There is a ring insulator between adjacent sub-rings. Each ring insulator has substantially the same internal radius as the sub-rings.

In another embodiment, a spectrometer is provided which includes a housing. The housing has a first end and a second end. Inside the housing are a substance of interest inlet (e.g., a membrane inlet), at least one gas inlet, a plurality of electrical contacts, an ionization source, and ring electrode, and an anode. The substance of interest inlet is adapted to receive molecules. The gas inlet is adapted to receive air and a dopant. The ionization source is adapted to create ions; and is in communication with the substance of interest inlet and in proximity to the first end. The anode is adapted to collect ions and is in proximity to the second end. The ring electrode in the housing includes a plurality of sub-rings adapted to provide an electric field inside the spectrometer. The sub-rings have an internal radius and a ring insulator between adjacent sub-rings. Each ring insulator has substantially the same internal radius as the sub-rings. The apparatus utilizes a gas exhaust in the housing for expelling contaminants and/or ions.

Other embodiments are also provided in which computer-readable mediums, apparatuses and systems perform similar features recited by the above methods.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures.

DETAILED DESCRIPTION

In the following description, numerous specific details are set forth to provide a more thorough understanding of the invention. As will be apparent to those skilled in the art, however, various changes using different configurations may be made without departing from the scope of the invention. In other instances, well-known features have not been described in order to avoid obscuring the invention. Thus, the invention is not considered limited to the particular illustrative embodiments shown in the specification and all such alternate embodiments are intended to be included in the scope of the appended claims. For example, aspects of this disclosure depict and describe the inlet that receives vapors from a substance of interest as a membrane inlet. However, those depictions and descriptions are for illustrative purposes.

Figure 1:
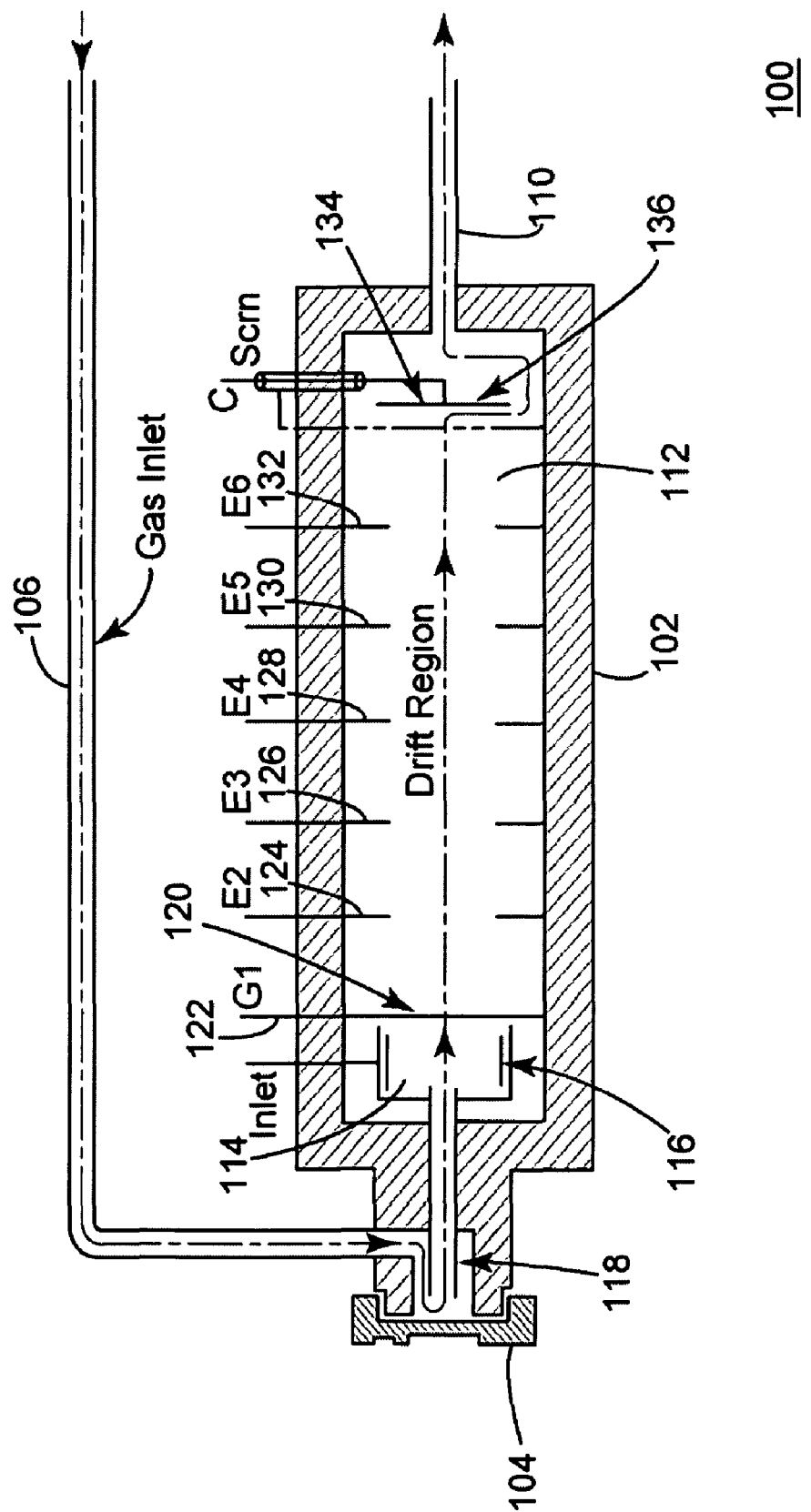
FIG. 1 is a prior art ion spectrometer.
Figure 2:
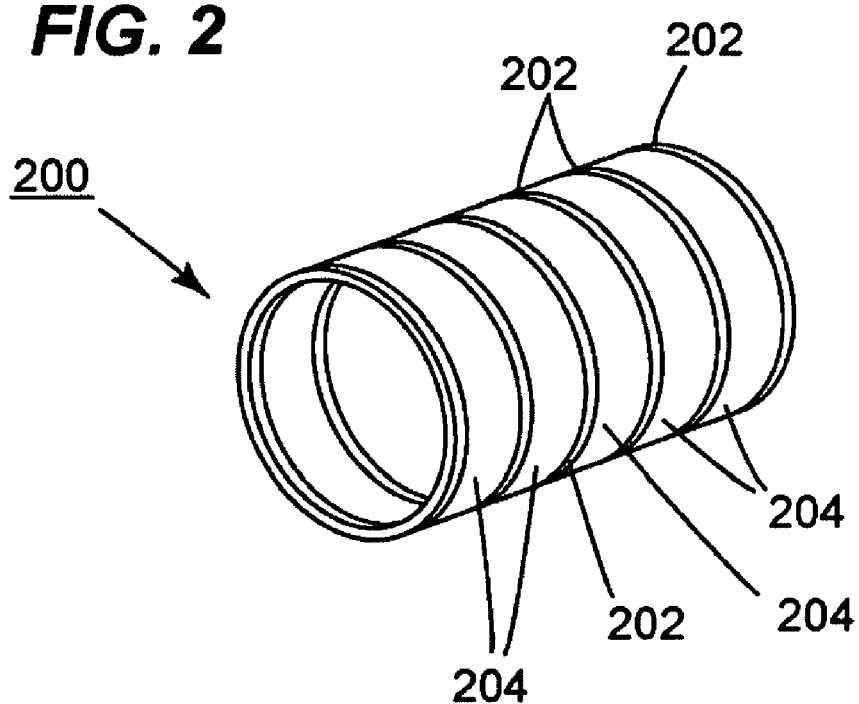
FIG. 2 is an embodiment of an exemplary ring electrode in accordance with aspects disclosed herein.

FIG. 2 is an embodiment of an exemplary ring electrode 200 in accordance with aspects disclosed herein. The ring electrode 200 includes a plurality of individual sub-ring shaped electrodes ("sub-rings") 204; and individual ring insulators 202. The ring insulators 202 separate adjacent sub-rings 204. The ring insulators 202 and sub-rings 204 have substantially the same internal diameter (also referred to herein as an "internal radius"). As a result, the interior surface of the ring electrode 200 is substantially smooth. One of the technical effects of the substantially smooth interior surface is that the likelihood of contaminants being trapped between the sub-rings 204 is significantly diminished. Because there is little or no space between the sub-rings 204, the time required to flush unwanted gases and contaminates (also referred to herein as the "clear-down time") is decreased.

The ring insulators 202 are made of any non-conductive material able to withstand temperatures within the spectrometer (e.g., ceramic, glass, quartz, or high temperature resistant plastic).

Although FIG. 2 depicts the ring electrode 200 having 5 sub-rings 204 and 6 ring insulators 202 there-between that depiction is for illustrative purposes only. It is appreciated that more or less sub-rings 204 and ring insulators 202 can be used in accordance with this disclosure. For example, about 4 to about 9 sub-rings 204 (and ring insulators 202 there-between) can be used. Increasing the number of sub-rings 204 increases resolution and sensitivity of the spectrometer.

Figure 3:
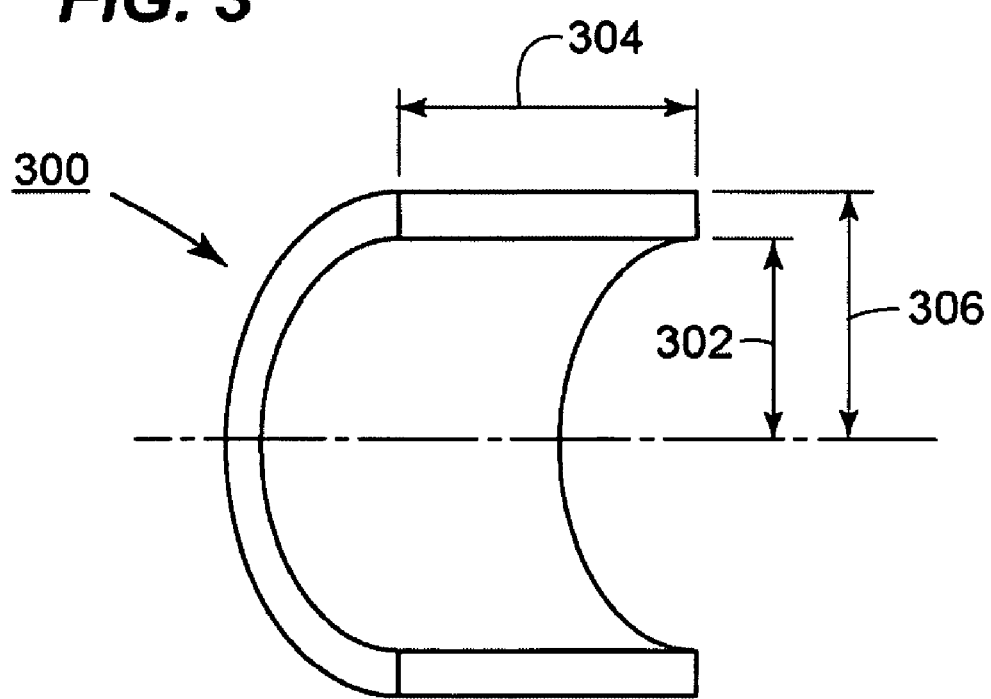
FIG. 3 depicts a cross-sectional view of an exemplary embodiment of a ring.

FIG. 3 depicts a cross-sectional view of an exemplary embodiment of a single sub-ring electrode 300. The sub-ring electrode 300 has an internal radius ("r") 302, a width ("w") 304, and an external radius ("R") 306. A sub-ring as used herein is generally defined as a solid having a volume calculated using Equation 1 below.

$$\text{Volume of Ring} = \pi(R^2 - r^2)w \qquad \text{Equation (1)}$$

where (R−r) is a number smaller than w. To provide the ring electrode 200 with a substantially smooth interior surface, the sub-rings 204 have the same internal radius r as the ring insulators 202.

Figure 4:
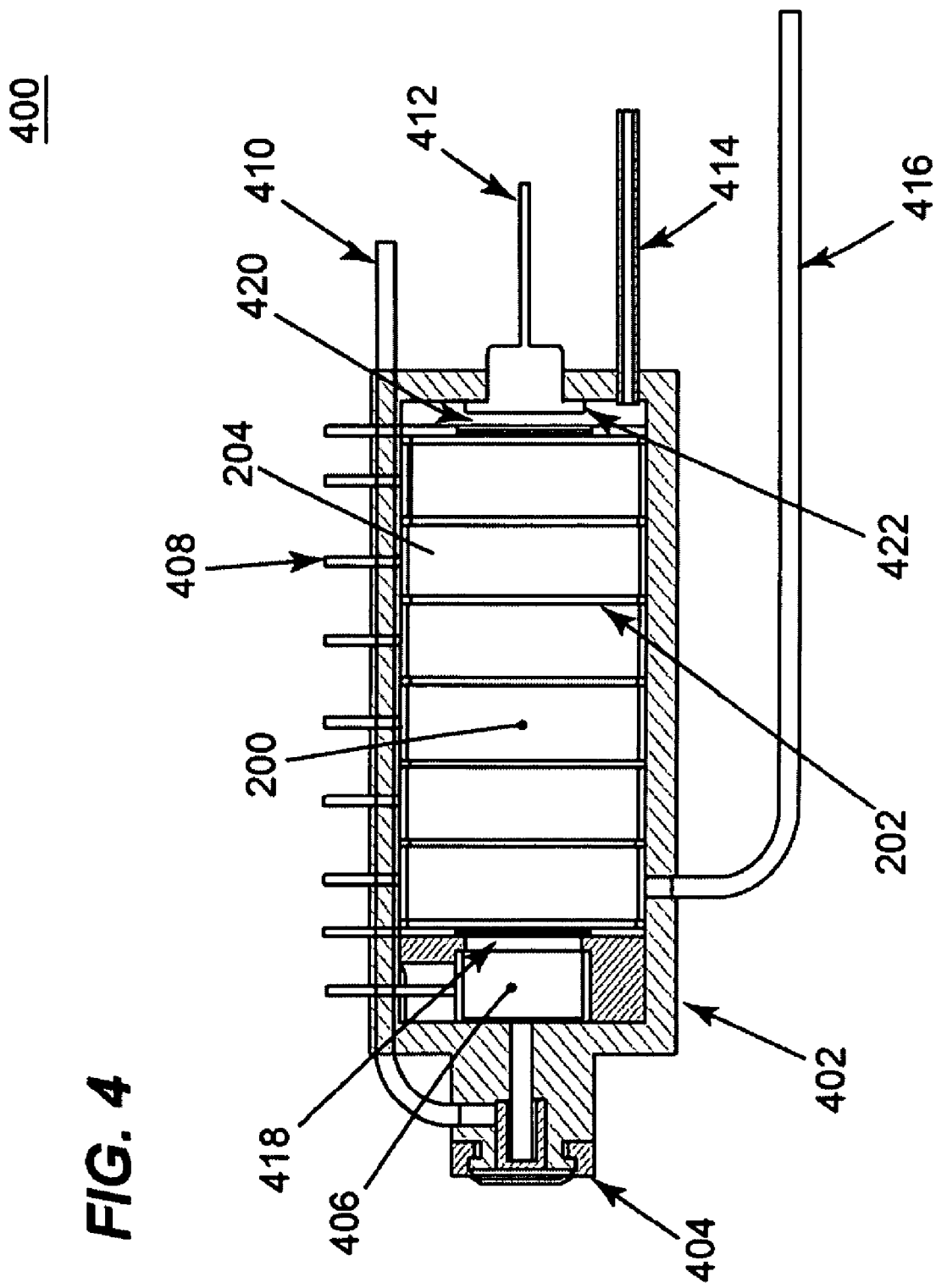
FIG. 4 depicts a cross-sectional view of an embodiment of an exemplary ion spectrometer, which utilizes the exemplary ring electrode disclosed in FIG. 2.

FIG. 4 depicts a cross-sectional view of an embodiment of an exemplary ion spectrometer 400, which utilizes the exemplary ring electrode disclosed in FIG. 2. The spectrometer 400 includes housing 402, a membrane 404, an ionization region 406, a ring electrode 200, electrical contacts 408, a membrane gas inlet 410, an anode electrical wire 412, a drift gas inlet 414, a perforated ion grid 418, a perforated anode grid 420, anode 422, and an exhaust gas outlet 416.

The ion spectrometer 400 includes a housing 402. The membrane gas inlet 410 is a conduit that allows air and a dopant (e.g., ammonia and/or methylene chloride) into the housing 402. The membrane gas with substances of interest (e.g., explosives or narcotics) that have permeated the membrane 404 pass into the ionization region 406. The membrane gas inlet 410 allows the air and dopant to force vapors of a substance to enter the ionization region 406 for subsequent testing.

The drift gas inlet 414 is a conduit that also allows air and the dopant (e.g., ammonia and/or methylene chloride) into the housing 402. However, the injection of air and dopant, via the drift gas inlet 414, is done so on an opposite end of the housing 402 (i.e., for injection of air and dopant past the anode screen grid 420 and into the drift region).

When a substance of interest (e.g., explosives, narcotics, and the like) is placed against a heated semi-permeable membrane 404 (e.g., via a swab), the chemical(s) is turned into a vapor. The vapor permeates the membrane 404 while the membrane 404 helps to keep out contaminants (e.g., water).

Air and dopant, provided via the first drift gas inlet 410, forces the vapor towards the ionization chamber 406. While in the ionization chamber 406, the vapor is ionized (e.g., ionization is induced either electrically or by a radioactive material (e.g., nickel 63 or tritium)).

A population of the ions builds up in the ionization chamber 406. An applied voltage pushes the ions through the ion grid 418 and into the drift region.

The ring electrode (e.g., ring electrode 200) is located inside the housing 402 to provide an electrical field inside the drift region. As such, the drift region is a single unobstructed cavity (i.e., the entire interior of the ring electrode). After the ions have been ionized in the ionization region, the voltage at 418 is varied to allow the flow of ions through the drift region. The electrical contacts 408 contact the sub-rings 204 that form the ring electrode 200 and allow the voltages to pass to each respective sub-ring 204 in the ring electrode 200.

Ring insulators 202 prevent physical and electrical contact between the sub-rings 204. In addition, the ring insulators 202 have substantially the same interior diameter (and radius about a central longitudinal axis) as that of the sub-rings 204, which decreases the likelihood of substances being trapped between the sub-rings 204.

The charged ring electrode 200 accelerates the ions towards the anode 422. The anode 422 collects the ions for subsequent analysis by a computer.

As the ions are collected, the drift region is flushed of the analyzed gas and ions, via the exhaust gas outlet 416. Because the area upon which the gases are expelled is unobstructed, the drift region can be flushed in a shorter time-span than if disk shaped electrodes were used. Some of the additional benefits of the ring electrode (i.e., the unobstructed interior of the ring electrode and drift region) are a shorter burn in time (i.e., a time-span shorter than a configuration that uses disk shaped electrodes or electrodes that protrude into the drift region) during construction of the spectrometer 400; and a more uniform electrical field (e.g., no eddy currents).

Although the ion spectrometer 100 utilizes a disk shaped electrodes, the ion spectrometer 100 can be modified or retrofitted (i.e., by removal of the disk shaped electrodes) to utilize ring electrode 200.

While the foregoing is directed to embodiments of the present invention, other and further embodiments of the invention may be devised without departing from the basic scope thereof, and the scope thereof is determined by the claims that follow.

What is claimed is:

1. A ring electrode comprising:
    a plurality of sub-rings adapted to provide an electric field inside a spectrometer, wherein each sub-ring of said plurality of sub-rings has an internal sub-ring radius, an external sub-ring radius, and a width, and wherein said width is greater than a difference between said external sub-ring radius and said internal sub-ring radius; and
    a ring insulator between adjacent sub-rings in said plurality, wherein each said ring insulator has an internal ring insulator radius substantially equal to said internal sub-ring radius.

2. The ring electrode of claim 1, wherein each said ring insulator comprises an insulating material, and wherein a width of said ring insulator is less than a width of each said sub-ring.

3. The ring electrode of claim 2, wherein said insulating material comprises one of glass, quartz, ceramic, and heat resistant plastic.

4. An apparatus comprising:
    a housing, said housing having a first end and a second end;
    a substance of interest inlet in said housing for receiving molecules;
    at least one gas inlet in said housing for receiving air and a dopant;
    a plurality of electrical contacts in said housing;
    an ionization source for creating ions in communication with said substance of interest inlet and positioned inside said housing and in proximity to said first end;
    an anode inside said housing and in proximity to said second end, said anode is adapted to collect said ions;
    a ring electrode in said housing comprising:
        a plurality of sub-rings adapted to provide an electric field inside a spectrometer, wherein each sub-ring of said plurality of sub-rings has an internal sub-ring radius, an external sub-ring radius, and a width, and wherein said width is greater than a difference between said external sub-ring radius and said internal sub-ring radius; and
        a ring insulator between adjacent sub-rings in said plurality, wherein each said ring insulator has an internal ring insulator radius substantially equal to said internal sub-ring radius; and
    a gas exhaust in said housing.

5. The apparatus of claim 4, wherein said plurality comprises at least 4 sub-rings, and wherein a width of said ring insulator is less than a width of each said sub-ring.

6. A method of producing an ion spectrometer comprising:
    inserting a plurality of sub-rings into a housing, wherein each sub-ring of said plurality of sub-rings has an internal sub-ring radius, an external sub-ring radius, and a width, and wherein said width is greater than a difference between said external sub-ring radius and said internal sub-ring radius; and
    inserting ring insulators between each sub-ring in said plurality, wherein each said ring insulator has an internal ring insulator radius substantially equal to said internal sub-ring radius.

7. The ring electrode of claim 1, wherein said plurality of sub-rings comprises at least 4 sub-rings, and wherein a width of each said ring insulator is less than a width of the each said sub-ring.

* * * * *